United States Patent [19]

Malamas

[11] Patent Number: 5,399,588
[45] Date of Patent: Mar. 21, 1995

[54] NAPHTHALENYLMETHYL CYCLOALKENONE ACETIC ACIDS AND ANALOGS THEREOF USEFUL AS ALDOSE REDUCTASE INHIBITORS

[75] Inventor: Michael S. Malamas, Jamison, Pa.

[73] Assignee: American Home Products Corporation, Madison, N.J.

[21] Appl. No.: 167,376

[22] Filed: Dec. 14, 1993

[51] Int. Cl.$^6$ .................................. A61K 31/557
[52] U.S. Cl. .................. 514/530; 514/541; 514/569; 562/462; 560/28
[58] Field of Search ............ 562/462; 560/28; 514/530, 541, 569

[56] References Cited

U.S. PATENT DOCUMENTS

| | | | |
|---|---|---|---|
| 4,897,405 | 1/1990 | Alessi | 514/360 |
| 5,183,825 | 2/1993 | Kees | 514/404 |

OTHER PUBLICATIONS

Beilstein 2626759, 1964.

*Primary Examiner*—José G. Dees
*Assistant Examiner*—Samuel Barts
*Attorney, Agent, or Firm*—R. F. Boswell, Jr.

[57] ABSTRACT

The compounds of this invention which have the formula:

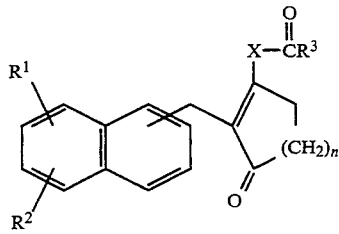

wherein:
R$^1$ and R$^2$ are independently hydrogen, C$_1$–C$_8$ alkyl, halogen, C$_1$–C$_8$ alkoxy, or trifluoromethyl;
R$^3$ is —OH or —NHCO$_2$CH$_3$;
X is —CH$_2$— or —OCH$_2$—;
n is 1 or 2;
or a pharmaceutically acceptable salt thereof, are useful in treating or inhibiting the long-term complications of diabetes such as diabetic retinopathy, nephropathy and neuropathy through the inhibition of the enzyme aldose reductase. Aldose reductase inhibitors have been shown to prevent the biochemical, functional and morphological changes induced by hyperglycemia.

3 Claims, No Drawings

NAPHTHALENYLMETHYL CYCLOALKENONE ACETIC ACIDS AND ANALOGS THEREOF USEFUL AS ALDOSE REDUCTASE INHIBITORS

FIELD OF THE INVENTION

This invention relates to naphthalenylmethyl cycloalkenone acetic acids, their analogs thereof, their pharmaceutically acceptable salts, to processes for their preparation, to methods for using the compounds, and to pharmaceutical preparations thereof. The compounds have pharmaceutical properties which render them beneficial for the prevention or treatment of complications associated with diabetes mellitus.

The use of insulin and/or oral hypoglycemic agents in the treatment of diabetes mellitus has prolonged the life of many of these patients. However, their use has not had a demonstrable impact on the development of diabetic complications such as neuropathy, nephropathy, retinopathy, cataracts and vascular disease which accompany the underlying metabolic disorder. There is little question that chronic hyperglycemia plays a major role in the genesis of these complications, and that complete normalization of blood glucose would likely prevent most if not all complications. For a number of reasons, though, chronic normalization of blood glucose has not been achieved with the currently available therapies.

BACKGROUND OF THE INVENTION

The long-term complications of diabetes develop in tissues where glucose uptake is independent of insulin. In these tissues, which include the lens, retina, kidney and peripheral nerves, the systemic hyperglycemia of diabetes is rapidly transposed into high tissular concentrations of glucose. In all of these tissues this excess glucose is rapidly metabolized by the sorbitol pathway. The intense diabetes-induced flux of glucose through this pathway appears to initiate a cascade of biochemical alterations which slowly progress to cell dysfunction and structural damage. Aldose reductase, the key enzyme in the sorbitol pathway, reduces glucose to sorbitol at the expense of the cofactor NADPH. In animal models of diabetes, compounds which inhibit aldose reductase have been shown to prevent the biochemical, functional and morphological changes induced by hyperglycemia. Early studies by J. H. Kinoshita and collaborators implicated aldose reductase in the etiology of diabetic cataracts. More recent studies have provided compelling evidence that aldose reductase also plays a significant role in the initiation of diabetic nephropathy, retinopathy and neuropathy [c.f. McCaleb et al, J. Diab. Comp., 2, 16, (1989); Robison et al, Invest. Ophthalmol. Vis. Sci., 30, 2285, (1989); and Notvest and Inserra, Diabetes, 36, 500, (1987)].

SUMMARY OF INVENTION

The naphthalenylmethyl cycloalkenone acetic acids and analogs thereof of the present invention are represented by formula (I).

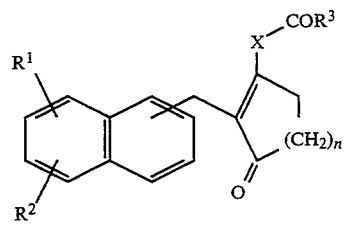

Wherein:
$R^1$, $R^2$ are independently hydrogen, $C_1$–$C_8$ alkyl, halogen, $C_1$–$C_8$ alkoxy, or trifluoromethyl;
$R^3$ is —OH or —NHCO$_2$CH$_3$;
X is —CH$_2$— or —OCH$_2$—;
n is 1 or 2;
or a pharmaceutically acceptable salt thereof.

The most preferred compounds of the present invention are set forth below:

[2-(5-bromo-naphthalen-2-ylmethyl)-3-oxo-cyclohex-1-enyl]-acetic acid,

[2-(5-bromo-6-methoxy-naphthalen-2-ylmethyl)-3-oxo-cyclohex-1-enyl]-acetic acid,

[2-(5-chloro-naphthalen-2-ylmethyl)-3-oxo-cyclohex-1-enyl]-acetic acid,

[2-(5-chloro-naphthalen-2-ylmethyl)-3-oxo-cyclopent-1-enyl]-acetic acid,

[[2-(5-bromo-naphthalen-2-ylmethyl)-3-oxo-cyclohex-1-enyl]-acetyl]carbamic acid methyl ester,

[2-[2-(5-chloro-naphthalen-2-ylmethyl)-3-oxo-cyclopent-1-enyl]-acetyl]carbamic acid methyl ester,

[2-(naphthalen-2-ylmethyl)-3-oxo-cyclohex-1-enyl]-acetic acid,

[[2-(5-chloro-naphthalen-2-ylmethyl)-3-oxo-1-cyclohex-1-enyl]oxy]-acetic acid,

[[2-(naphthalen-2-ylmethyl)-3-oxo-1-cyclohex-1-enyl]oxy]-acetic acid,

[[2-(5-bromo-naphthalen-2-ylmethyl)-3-oxo-cyclohex-1-enyl]oxy]-acetic acid,

[[2-(5-chloro-naphthalen-2-ylmethyl)-3-oxo-cyclopent-1-enyl]oxy]-acetic acid,

[[2-(2-naphthalen-2-ylmethyl)-3-oxo-cyclopent-1-enyl]oxy]-acetic acid,

[2-(6-methoxy-5-trifluoromethyl-naphthalen-1-ylmethyl)-3-oxo-cyclohex-1-enyl]-acetic acid, and

[2-(6-methoxy-5-trifluoromethyl-naphthalen-1-ylmethyl)-3-oxo-cyclopent-1-enyl]-acetic acid.

By way of further definition of terms, the term $C_1$–$C_8$ alkyl includes both straight and branched chain hydrocarbon radicals of up to 8 carbons such as methyl, ethyl, propyl, isopropyl, butyl, tert-butyl, pentyl, neopentyl, hexyl, heptyl, or octyl. The term halogen refers to a fluorine, chlorine, bromine, or iodine radical. The term $C_1$–$C_8$ alkoxy refers to an —O—$C_1$–$C_8$ alkyl group where the $C_1$–$C_8$ alkyl group is as defined above. The term pharmaceutically acceptable salt refers to solvates, hydrates and addition salts formed from an invention compound and a pharmaceutically acceptable base. The chemical bases wihch can be reacted with the various acidic cycloalkenone acetic acids and acetyl carbamates described herein to prepare the pharmaceutically acceptable salts are those which form non-toxic salts. These particular non-toxic base salts are such a nature that their cations are said to be essentially non-toxic in character over a wide range of dosage administered.

Suitable bases are the alkali metal hydroxides (sodium or potassium), the alkali earth metal hydroxides (calcium or magnesium), ammonia, or primary or secondary alkyl amines. These salts can easily be prepared by simply treating the invention compounds with an aqueous or alcoholic solution of the pharmaceutically acceptable base and then isolating the salt formed by filtration or evaporation of the solvent. The salts are administered usually in the same manner as the parent compound.

A method is provided for preventing or relieving diabetes mellitus associated complications in a diabetic mammal by administering to said mammal a prophylactic or alleviating amount of the compounds of formula (I). Such complications include neuropathy, nephropathy, retinopathy, keratopathy, diabetic uveitis, cataracts and limited joint mobility.

The compounds of formula (I), when admixed with a pharmaceutically acceptable carrier, form a pharmaceutical composition which can be used according to the preceding method.

DETAILED DESCRIPTION OF THE INVENTION

The Process

The naphthalenylmethyl cycloalkenone acetic acids and analogs thereof of the present invention were prepared by the following synthetic reaction scheme. In the following scheme $R^1$, $R^2$ and n are as defined under Formula I above.

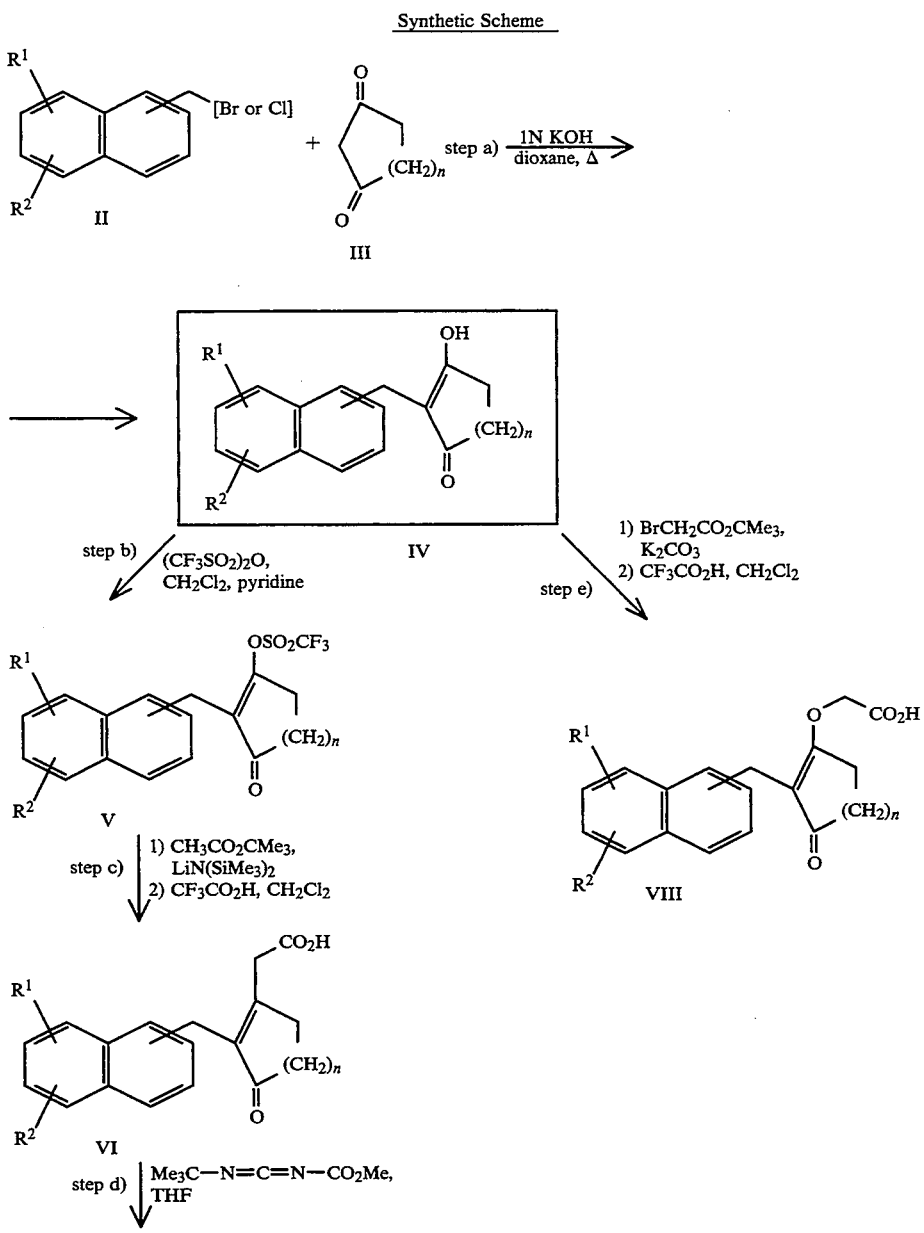

-continued
Synthetic Scheme

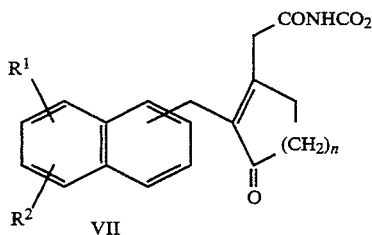

VII

The starting materials used in the synthetic scheme can be purchased commercially or prepared by known methods conventional in the art. The N-methoxycarbonyl-N'-tert-butylcarbodiimide used for the preparation of the acetylcarbamic acid methyl ester analogs was prepared according to the known synthetic method [Bulletin of the Chemical Society of Japan, 45, 3607–3611, (1972)]. The bromo(or chloro)methyl naphthalenes (II) are either commercially available, prepared according to procedures given in the following specific examples, or prepared according to procedures disclosed in our commonly owned U.S. Pat. Nos. 4,897,405 and 5,183,825 which are herein incorporated by reference.

A general description of the process for the production of the compounds of formula (I), wherein $R^1$, $R^2$, $R^3$, X, and n are as defined above, comprises:

Step a) Reacting either a 1- or 2-(bromomethyl)naphthalene or 1- or 2-(chloromethyl)naphthalene of formula (II) with 1,3-cycloalkyldiones of formula (III) in the presence of a base, such as potassium hydroxide, in a conventional solvent which does not adversely influence the reaction, for example, dioxane, to produce the compound of formula (IV).

Step b) The compound of formula (IV) can be reacted with trifluoromethanesulfonic anhydride in the presence of pyridine, in a conventional solvent which does not adversely influence the reaction, for example, dichloromethane, to produce the compound of formula (V).

Step c) The compound of formula (V) can be reacted with the lithium enolate of tert-butyl acetate (which lithium enolate was prepared from tert-butyl acetate and lithium bis(trimethylsilyl)amide in tetrahydrofuran), in a conventional solvent which does not adversely influence the reaction, for example, tetrahydrofuran, followed by acidic hydrolysis with an organic or inorganic acid, for example trifluoroacetic acid, to produce the compound of formula (VI) which is a compound according to formula (I) wherein $R^3$ is —OH.

Step d) Compound of formula (VI) can be reacted with N-methoxycarbonyl-N'-tert-butylcarbodiimide, in a conventional solvent which does not adversely influence the reaction, for example, tetrahydrofuran, to produce the compound of formula (VII) which is a compound according to formula (I) wherein $R^3$ is —NHCO$_2$Me.

Step e) Compound of formula (IV) can be reacted with tert-butyl bromoacetate, in the presence of a base, for example, potassium carbonate, in a conventional solvent which does not adversely influence the reaction, for example, N,N-dimethylformamide, followed by acidic hydrolysis with an organic or inorganic acid, for example trifluoroacetic acid, to produce the compound of formula (VIII) which is a compound according to formula (I) wherein X is —OCH$_2$— and $R^3$ is —OH.

EXPERIMENTAL SECTION

The following examples show the preparation and the pharmacological testing of compounds within the invention.

EXAMPLE 1

[2-(5-Bromo-naphthalen-2-ylmethyl)-3-oxo-cyclohex-1-enyl]-acetic acid

Step a) 2-(5-bromo-naphthalen-2-ylmethyl)-3-hydroxy-2-cyclohexen-1-one

To a mixture of 5-bromo-2-chloromethylnaphthalene (17.0 g, 66.5 mmol), 1,3-cyclohexanedione (7.45 g, 66.5 mmol) and dioxane (150 mL) was added KOH (1N, 66.5 mL). The mixture was stirred at 75° C. for 24 hours, poured into H$_2$O and extracted with EtOAc. The volatiles were removed in vacuo, and the residue was treated with 2N NaOH and extracted with Et$_2$O. The aqueous layer was acidified with 2N HCl, extracted with EtOAc and dried over MgSO$_4$. Evaporation and crystallization from acetone/ether/hexane gave a white solid (11.5 g, 52% yield, m.p. 209°–210° C.).

Analysis for: $C_{17}H_{15}BrO_2$: Calc'd: C, 61.65; H, 4.66; Found.: C, 61.54; H, 4.43 .

step b) Trifluoromethanesulfonic acid 2-(5-bromo-naphthalen-2-ylmethyl)-3-oxo-cyclohex-1-enyl ester To a cold (0° C.) mixture of 2-(5-bromo-naphthalen-2-ylmethyl)-3-hydroxy-2-cyclohexen-1-one (6.0 g, 18.12 mmol) and anhydrous methylene chloride (100 mL) was added pyridine (2.2 mL, 27.18 mmol). After stirring for 10 minutes trifluoromethanesulfonic anhydride (3.12 mL, 19.02 mmol) was added dropwise. The mixture was stirred for 30 minutes, diluted in ether (200 mL) washed with aqueous NaHCO$_3$, H$_2$O and dried. The organic layer was dried over MgSO$_4$. Evaporation and purification by flash chromatography on silica gel (eluting solvent hexane/EtOAc 1/1) gave a viscous brownish oil (8.1 g, 96% yield).

Analysis for: $C_{18}H_{14}BrF_3O_4S$: Calc'd: C, 46.67; H, 3.05; Found: C, 46.66; H, 2.75.

Step c) [2-(5-bromo-naphthalen-2-ylmethyl)-3-oxo-cyclohex-1-enyl]-acetic acid

In to a cold (−78° C.) solution of tert-butyl acetate (2.7 mL, 19.96 mmol) in THF (35 mL) was added lithium bis(trimethylsilyl)amide solution (1.0M, 21.62 mL, 21.62 mmol). After stirring for 2 hours a solution of trifluoromethanesulfonic acid 2-(5-bromo-naphthalen-2-ylmethyl)-3-oxo-cyclohex-1-enyl ester (7.7 g, 16.63 mmol) in THF (15 mL) was added dropwise. The mixture was stirred for 1 hour, quenched with aqueous NH$_4$Cl, poured in to H$_2$O and extracted with EtOAc. The organic extracts were dried over MgSO$_4$. Evaporation gave a yellow oil residue which was taken up in methylene chloride (100 mL) and treated with trifluoroacetic acid (10 mL). The mixture was stirred for 5 hours and then the volatiles were removed in vacuo. The residue was purified by flash chromatography on acidic silica gel (eluting solvent hexane/EtOAc 1/1) to give a yellow solid (4.1 g, 66% yield, m.p 56°–58° C.).

Analysis for: $C_{19}H_{17}BrO_3$: Calc'd: C, 61.14; H, 4.59; Found: C, 61.02; H, 4.48.

EXAMPLE 2

[2-(5-bromo-6-methoxy-naphthalen-2-ylmethyl)-3-oxocyclohex-1-enyl] acetic acid

The title compound was prepared in substantially the same manner as described in Example 1, steps a–c, and was obtained as a yellow solid, m.p. 165°–166° C.

Analysis for: $C_{20}H_{19}BrO_4$: Calc'd: C, 59.27; H, 4.75; Found: C, 59.55; H, 4.71.

EXAMPLE 3

[2-(5-chloro-naphthalen-2-ylmethyl)-3-oxo-cyclohex-1-enyl]-acetic acid

The title compound was prepared in substantially the same manner as described in Example 1, steps a–c, and was obtained as a yellow solid, m.p. 98°–100° C.

Analysis for: $C_{19}H_{17}ClO_3$: Calc'd: C, 69.41; H, 5.21; Found: C, 69.71; H, 5.15.

EXAMPLE 4

[2-(5-chloro-naphthalen-2-ylmethyl)-3-oxo-cyclopen-1-enyl]-acetic acid

The title compound was prepared in substantially the same manner as described in Example 1, steps a–c. 1,3-Cyclopentanedione was used in place of 1,3-cyclohexanedione. The title compound was obtained as a yellow solid, m.p. 131°–132° C.

Analysis for: $C_{18}H_{15}ClO_3$: Calc'd: C, 68.68; H, 4.80; Found: C, 68.95; H, 4.65.

EXAMPLE 5

[[2-(5-bromo-naphthalen-2-ylmethyl)-3-oxo-cyclohex-1-enyl]acetyl]carbamic acid methyl ester A mixture of [2-(5-bromo-naphthalen-2-ylmethyl)-3-oxo-cyclohex-1-enyl]-acetic acid (1.1 g, 2.95 mmol), N-methoxycarbonyl-N'-tert-butylcarbodiimide (0.51 g, 3.25 mmol), and THF (20 mL) was refluxed for 4 hours. The volatiles were removed in vacuo and the residue was purified by flash chromatography on silica gel (eluting solvent hexane/EtOAc 2/1) to give a white solid (0.95 g, 76% yield, m.p. 128°–129° C.).

Analysis for: $C_{21}H_{20}BrNO_4$: Calc'd: C, 58.62; H, 4.68; N, 3.25; Found: C, 58.72; H, 4.44; N, 3.33.

EXAMPLE 6

[2-[2-(5-chloro-naphthalen-2-ylmethyl)-3-oxo-cyclopent-1-enyl]-acetyl]carbamic acid methyl ester The title compound was prepared in substantially the same manner as described in Example 5, and was obtained as a white solid m.p. 132°–134° C.

Analysis for: $C_{20}H_{18}ClNO_4$: Calc'd: C, 64.61; H, 4.88; N, 3.77; Found: C, 64.86; H, 4.79; N, 3.72.

EXAMPLE 7

[2-(naphthalen-2-ylmethyl)-3-oxo-cyclohex-1-enyl]-acetic acid

The title compound was prepared in substantially the same manner as described in Example 1, steps a–c, and was obtained as a yellow solid, m.p. 78°–80° C.

Analysis for: $C_{19}H_{18}O_3$; Calc'd: C, 77.53; H, 6.16; Found: C, 77.43; H, 6.10.

EXAMPLE 8

[[2-(5-chloro-naphthalen-2-ylmethyl)-3-oxo-1-cyclohex-1-enyl]oxy]acetic acid

A mixture of 2-(5-chloro-2-naphthalen-2-ylmethyl)-3-hydroxy-2-cyclohexen-1-one (2.3 g, 8.03 mmol), tert-butyl bromoacetate (1.94 mL, 16.0 mmol), potassium carbonate (2.2 g, 16.0 mmol) and DMF (40 mL) was stirred at 75° C. for 2 hours. The mixture was poured into $H_2O$ and extracted with EtOAc. The organic extracts were dried over $MgSO_4$. The volatiles were removed in vacuo and the residue was taken up in $CH_2Cl_2$ (50 mL) and treated with trifluoroacetic acid (10 mL). The mixture was stirred at room temperature for 5 hours. The volatiles were removed in vacuo and the crude product was crystallized from ether/hexane (after cooling to −20° C.) to give an off-white solid (1.85 g, 67%, yield, m.p. 236°–238° C.).

Analysis for: $C_{19}H_{17}ClO_4$: Calc'd: C, 66.19; H, 4.97; Found: C, 66.05; H, 4.92.

EXAMPLE 9

[[2-(naphthalen-2-ylmethyl)-3-oxo-1-cyclohex-1-enyl]oxy]acetic acid

The title compound was prepared in substantially the same manner as described in Example 8, and was obtained as a light pink solid, m.p. 170°–171° C.

Analysis for: $C_{19}H_{18}O_4$; Calc'd: C, 73.53; H, 5.85; Found: C, 73.22; H, 5.57.

EXAMPLE 10

[[2-(5-bromo-naphthalen-2-ylmethyl)-3-oxo-cyclohex-1-enyl]oxy]-acetic acid

The title compound was prepared in substantially the same manner as described in Example 8, and was obtained as a white solid, m.p. 234°–236° C.

Analysis for: $C_{19}H_7BrO_4$: Calc'd: C, 58.63; H, 4.40; Found: C, 58.30; H, 4.39.

EXAMPLE 11

[[2-(5-chloro-naphthalen-2-ylmethyl)-3-oxo-cyclopent-1-enyl]oxy]-acetic acid

The title compound was prepared in substantially the same manner as described in Example 8, and was obtained as a white solid, m.p. 156°–158° C.

Analysis for: $C_{18}H_5ClO_4$: Calc'd: C, 65.36; H, 4.57 ; Found: C, 65.17; H, 4.60.

EXAMPLE 12

[[2-(2-Naphthalen-2-ylmethyl)-3-oxo-cyclopent-1-enyl]oxy]-acetic acid

The title compound was prepared in substantially the same manner as described in Example 8, and was obtained as a white solid, m.p. 156°–158° C.

Analysis for: $C_{18}H_{16}O_4$: Calc'd: C, 7296; H, 5.44; Found: C, 72.84; H, 5.69.

EXAMPLE 13

[2-(6-methoxy-5-trifluoromethyl-naphthalen-1-ylmethyl)-3-oxo-cyclohex-1-enyl]-acetic acid The title compound was prepared in substantially the same manner as described in Example 1 steps a-c and was obtained as a yellow solid, m.p. 69°–71° C.

Analysis for: $C_{21}H_{19}F_3O_4$: Calc'd: C, 64.28; H, 4.88; Found: C, 63.97; H, 4.70.

EXAMPLE 14

[2-(6-Methoxy-5-trifluoromethyl-naphthalen-1-ylmethyl)-3-oxo-cyclopent-1-enyl]-acetic acid The title compound was prepared in substantially the same manner as described in Example 1 steps a-c, and was obtained as a yellow solid, m.p. 59°–61° C.

Analysis for: $C_{20}H_{17}F_3O_4$: Calc'd: C, 63.49; H, 4.53; Found: C, 63.31; H, 4.57.

The chloro (or bromo)methylnaphthalenes used in the above specific examples were prepared according to the following references or procedures.

6-methoxy-5-trifluoromethyl-1-bromomethylnaphthalene

Prepared according to reference: J. Med. Chem. 27, 255–256 (1984).

5-bromo-2-chloromethylnaphthalene and 5-chloro-2-chloromethylnaphthalene

Prepared according to references: J. Med. Chem. 36, 2485–2493 (1993); and U.S. Pat. No. 4,897,405 (1990).

5-Bromo-6-methoxy-2-bromomethylnaphthalene

Prepared according to the following steps.

6-Hydroxy-2-naphthaldehyde

Step a) N-Butyllithium (35.9 mL, 89.7 mmol) was added dropwise to a cold (−78° C.) solution of 6-bromo-2-naphthol (20.0 g, 89.7 mmol) in THF (200 mL). After stirring for 10 minutes, tert-butyllithium (52.76 mL, 89.7 mmol) was added dropwise. The mixture was stirred for 30 min at −78° C., and two hours at −20° C. Then, hexamethylphosphoramide (15.6 mL, 89.7 mmol) was added to the reaction mixture. After stirring for 20 minutes. N,N-dimethylformamide (6.94 mL, 89.7 mmol) was added dropwise. The mixture was allowed to come to room temperature, stirred for 1 hour, and quenched with aqueous ammonium chloride. The mixture was poured into water, acidified with 2N HCL and extracted with EtOAc. The organic extracts were dried over MgSO4. Evaporation and purification by flash chromatography (hexane/EtOAc 3/1 ), gave a yellow solid (12.5 g, 81% yield, m.p. 173°–174° C.).

Analysis for: $C_{11}H_8O_2$: Calc'd: C, 76.73; H, 4.68; Found: C, 76.96; H, 4.67.

5-Bromo-6-hydroxy-2-naphthldehyde

Step b) Bromine (7.45 mL, 145.3 mmol) was added dropwise to a cold (0° C.) solution of 6-hydroxy-2-naphthaldehyde (25.0 g. 145.3 mmol) in acetic acid (300 mL). After stirring for 30 minutes the mixture was poured into water (2 l), and the precipitated solid filtered and dried to yield a brown solid (34.5 g, 94% yield, m.p. 189–190).

Analysis for: $C_{11}H_7BrO_2$: Calc'd: C, 52.62; H, 2.81; Found: C, 52.22; H, 2.67.

5-Bromo-6-methoxy-2-naphthldehyde

Step c) A mixture of 5-bromo-6-hydroxy-2-naphthaldehyde (34.0 g, 135.5 mmol), potassium carbonate (18.7 g, 135.5 mmol), dimethyl sulfate (12.8 mL, 135.5 mmol) and acetone (500 mL), was refluxed for 3 hours. The volatiles were removed in vacuo, and the residue was suspended in water. The precipitated solid was filtered and dried, to yield a yellow solid (34.5 g, 96 % yield, m.p. 133°–135° C.).

Analysis for: $C_{12}H_9BrO_2$: Calc'd: C, 54.37; H, 3.42; Found: C, 54.76; H, 3.30.

5-Bromo-6-methoxy-2-naphthalenemethanol

Step d) Sodium borohydride (4.78 g, 128.3 mmol) was added portionwise in to a cold (0° C.) mixture of 5-bromo-6-methoxy-2-naphthldehyde (34.0 g, 128.3 mmol) in methanol (300 ml) and THF (200 mL). After stirring for 30 minutes the mixture was poured in to water and extracted with EtOAc. The organic extracts were dried over MgSO4. Evaporation and purification by flash chromatography (hexane/EtOAc 2/1) gave a yellow solid (30.5 g, 90% yield, m.p. 85°–87° C.).

Analysis for: $C_{12}H_{11}BrO_2$: Calc'd: C, 53.96; H, 4.15; Found: C, 54.20; H, 3.98.

5-Bromo-6-methoxy-2-bromomethylnaphthalene

Step e) A solution of 5-bromo-6-methoxy-2-naphthalenemethanol (29.4 g, 110.1 mmol) in ethyl ether (300 mL) was added slowly into a cold (0° C.) mixture of phosphorus pentachloride (34.5 g, 165.1 mmol), calcium carbonate (16.5 g, 165.1 mmol) and ethyl ether (300 mL). After stirring for 30 minutes the mixture was poured in to water and extracted with ethyl ehter. The organic extracts were dried over MgSO4. Evaporation and crystallization from ethyl ether/hexane, gave a yellow solid (30.4 g, 97% yield, m.p. 92°–94° C.).

Analysis for: $C_{12}H_{10}BrClO$: Calc'd: C, 50.47; H, 3.53; Found: C, 50.67; H, 3.36.

PHARMACOLOGY

I. In vivo Inhibition of Aldose Reductase in Galactosemic Rats

The aldose reductase inhibiting property of the compounds of this invention and the utilization of the compounds in preventing, diminishing and alleviating diabetic complications are demonstrable in experiments using galactosemic rats, see Dvornik et al., Science, 182, 1146 (1973).

(a) Four or more groups of six male rats, 50–70 g, Sprague-Dawley strain, were used. The first group, the control group, was fed a mixture of laboratory chow (rodent Laboratory Chow, Purina) and glucose at 20% (w/w %) concentration. An untreated galactosemic group was fed a similar diet in which galactose was substituted for glucose. The third group was fed a diet prepared by mixing a given amount of the test compound with the galactose containing diet. The concentration of galactose in the diet of the treated groups was the same as that for the untreated galactosemic group.

(b) After four days, the animals were killed by euthanization. Both the lens and sciatic nerve were removed, weighed and stored frozen for polyol determination.

(c) The polyol determination was performed by a modification of the procedure of M. Kraml and L. Cosyns, Clin. Biochem., 2, 373 (1969). Only two minor reagent changes were made: (a) the rinsing mixture was an aqueous 5% (w/v) trichloroacetic acid solution and (b) the stock solution was prepared by dissolving 25 mg of dulcitol in 100 mL of an aqueous trichloroacetic acid solution. [N.B.: For each experiment the average value found in the tissue from rats fed the glucose diet was subtracted from the individual values found in the corresponding tissue in galactose-fed rats to obtain the amount of polyol accumulated].

The results for compounds of this invention tested in this assay are presented in Table 1.

TABLE 1

| Compound of Example No. | Dose (mg/kg/day) | % Inhibition of aldose reductase |
|---|---|---|
| 1 | 100 | 68 |
| 2 | 100 | 71 |
| 3 | 202 | 73 |
| 3 | 105 | 52 |
| 4 | 100 | 37 |
| 5 | 100 | 45 |

II. In vitro Inhibition of Aldose Reductase in the Bovine Lens

The aldose reductase inhibiting effects of the compounds of formula (I) were also tested by employing an in vitro testing procedure similar to that described by S. Hayman and J. H. Kinoshita, J. Biol. Chem., 240, 877 (1965) wherein the ability of the invention compounds to inhibit bovine lens aldose reductase with DL-glyceraldehyde as the substrate was determined. In the present case the procedure of Hayman and Kinoshita was modified in that the final chromatography step was omitted in the preparation of the enzyme from bovine lens.

The results for compounds of this invention tested in this assay are presented in Table 2.

TABLE 2

| Compound of Example No. | Dose (M) | % Inhibition of aldose reductase |
|---|---|---|
| 1 | $4 \times 10^{-8}$ | 78 |
| 2 | $10^{-7}$ | 50 |
| 3 | $4 \times 10^{-8}$ | 79 |
| 4 | $4 \times 10^{-8}$ | 62 |
| 5 | $10^{-5}$ | 27 |
| 6 | $10^{-5}$ | 19 |
| 7 | $10^{-6}$ | 41 |
| 8 | $4 \times 10^{-8}$ | 81 |
| 9 | $10^{-6}$ | 87 |
| 10 | $4 \times 10^{-8}$ | 86 |
| 11 | $4 \times 10^{-8}$ | 70 |
| 12 | $10^{-6}$ | 61 |
| 13 | $10^{-5}$ | 51 |
| 14 | $10^{-5}$ | 84 |

PHARMACEUTICAL COMPOSITION

The naphthalenylmethyl cycloalkenone acetic acids and their analogs thereof, of this invention may be administered to mammals, for example, man, cattle, or rabbits, either alone or in dosage forms, i.e., capsules or tablets, combined with pharmacologically acceptable excipients.

The compounds of this invention may be given orally. However, the method of administering the present active ingredients of this invention is not to be construed as limited to a particular mode of administration. For example, the compounds may be administered topically directly to the eye in the form of drops of sterile, buffered ophthalmic solutions, preferably of pH 7.2–7.6. Also, they may be administered orally in solid form containing such excipients as starch, milk sugar, certain types of clay and so forth. They may also be administered orally in the form of solutions or they may be injected parenterally. For parenteral administration, they may be used in the form of a sterile solution, preferably of pH 7.2–7.6, containing a pharmaceutically acceptable buffer.

The dosage of the naphthalenylmethyl cycloalkenone acetic acids and their analogs thereof, will vary with the form of administration and the particular compound chosen. Furthermore, it will vary with the particular host under treatment. Generally, treatment is initiated with small dosages substantially less than the optimal dose of the compound. Thereafter, the dosage is increased by small increments until efficacy is obtained. In general, the compounds of this invention are most desirably administered at a concentration level that will generally afford effective results without causing any harmful or deleterious side effects. For topical administration, a 0.05–1.0% solution may be administered dropwise in the eye. The frequency of instillation varies with the subject under treatment from a drop every two or three days to once daily. For oral or parenteral administration a preferred level of dosage ranges from about 0.05 mg to about 250 mg per kilo of body weight per day, although aforementioned variations will occur. However, a dosage level that is in the range of from about 0.05 mg to about 50 mg per kilo of body weight per day is most satisfactory. Obviously, one or more unit doses can be administered one or more times per day to achieve the desired therapeutic effect.

Unit dosage forms such as capsules, tablets, pills and the like may contain from about 1.0 mg to about 250 mg of the active ingredients of this invention with a pharmaceutical carder. Thus, for oral administration, capsules can contain from between about 1.0 mg to about 250 mg of the active ingredients of this invention with or without a pharmaceutical diluent. Tablets, either effervescent or noneffervescent, can contain between about 1.0 to 250 mg of the active ingredients of this invention together with conventional pharmaceutical carriers. Thus tablets, which may be coated and either effervescent or noneffervescent, may be prepared according to the known art. Inert diluents or carriers, for example, magnesium carbonate or lactose, can be used together with conventional disintegrating agents for example, magnesium stearate.

The naphthalenylmethyl cycloalkenone acetic acids and their analogs thereof, also can be used in combination with insulin or oral hypoglycemic agents to produce a beneficial effect in the treatment of diabetes mellitus. In this instance, commercially available insulin preparations or oral hypoglycemic agents, exemplified by acetohexamide, chlorpropamide, tolazamide, tolbutamide and phenformin, are suitable. The compounds hereof can be administered sequentially or simultaneously with insulin or the oral hypoglycemic agent. Suitable methods of administration, compositions and doses of the insulin preparation or oral hypoglycemic agent are described in medical textbooks; for instance, *Physicians' Desk Reference*, 47th ed., Medical Economics Co., Oradell, N.J., U.S.A., 1993.

What is claimed is:

1. A compound having the formula:

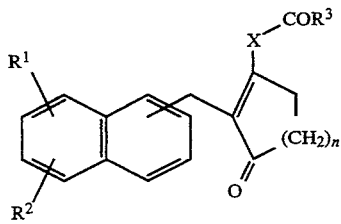

wherein:

$R^1$, $R^2$ are independently hydrogen, $C_1$–$C_8$ alkyl, halogen, $C_1$–$C_8$ alkoxy, or trifluoromethyl;
$R^3$ is —OH or —NHCO$_2$CH$_3$;
X is —CH$_2$— or —OCH$_2$—;
n is 1 or 2;

or a pharmaceutically acceptable salt thereof.

2. A compound according to claim 1 selected from the group consisting of:
[2-(5-bromo-naphthalen-2-ylmethyl)-3-oxo-cyclohex-1-enyl]-acetic acid,
[2-(5-bromo-6-methoxy-naphthalen-2-ylmethyl)-3-oxo-cyclohex-1-enyl]-acetic acid,
[2-(5-chloro-naphthalen-2-ylmethyl)-3-oxo-cyclohex-1-enyl]-acetic acid,
[2-(5-chloro-naphthalen-2-ylmethyl)-3-oxo-cyclopent-1-enyl]-acetic acid,
[[2-(5-bromo-naphthalen-2-ylmethyl)-3-oxo-cyclohex-1-enyl]-acetyl]carbamic acid methyl ester,
[2-[2-(5-chloro-naphthalen-2-ylmethyl)-3-oxo-cyclopent-1-enyl]-acetyl]carbamic acid methyl ester,
[2-(naphthalen-2-ylmethyl)-3-oxo-cyclohex-1-enyl]-acetic acid,
[[2-(5-chloro-naphthalen-2-ylmethyl)-3-oxo-1-cyclohex-1-enyl]oxy]-acetic acid,
[[2-(naphthalen-2-ylmethyl)-3-oxo-1-cyclohex-1-enyl]oxy]-acetic acid,
[[2-(5-bromo-naphthalen-2-ylmethyl)-3-oxo-cyclohex-1-enyl]oxy]-acetic acid,
[[2-(5-chloro-naphthalen-2-ylmethyl)-3-oxo-cyclopent-1-enyl]oxy]-acetic acid,
[[2-(2-naphthalen-2-ylmethyl)-3-oxo-cyclopent-1-enyl]oxy]-acetic acid,
[2-(6-methoxy-5-trifluoromethyl-naphthalen-1-ylmethyl)-3-oxo-cyclohex-1-enyl]-acetic acid,
and
[2-(6-methoxy-5-trifluoromethyl-naphthalen-1-ylmethyl)-3-oxo-cyclopent-1-enyl]-acetic acid.

3. A pharmaceutical composition for the treatment or prevention of diabetic complications in a diabetic mammal which comprises a pharmaceutical carrier and a therapeutically effective amount of a compound having the formula:

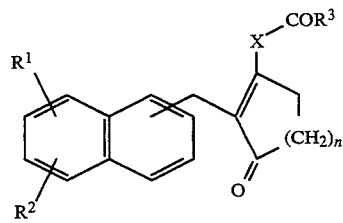

wherein:

$R^1$, $R^2$ are independently hydrogen, $C_1$–$C_8$ alkyl, halogen, $C_1$–$C_8$ alkoxy, or trifluoromethyl;
$R^3$ is —OH or —NHCO$_2$CH$_3$;
X is —CH$_2$— or —OCH$_2$—;
n is 1 or 2;
or a pharmaceutically acceptable salt thereof.

* * * * *